(12) United States Patent
Anthony et al.

(10) Patent No.: US 6,393,384 B1
(45) Date of Patent: May 21, 2002

(54) APPARATUS AND METHOD FOR REMOTE ULTRASONIC DETERMINATION OF THIN MATERIAL PROPERTIES USING SIGNAL CORRELATION

(75) Inventors: Brian W. Anthony, Cambridge; Petros A. Kotidis, Framingham; Daniel E. Klimek, Lexington; Agostino Abbate, Boxborough, all of MA (US)

(73) Assignee: Textron Systems Corporation, Wilmington, DE (US)

( * ) Notice: Subject to any disclaimer, the term of this patent is extended or adjusted under 35 U.S.C. 154(b) by 0 days.

(21) Appl. No.: 09/288,887

(22) Filed: Apr. 9, 1999

Related U.S. Application Data

(60) Provisional application No. 60/081,312, filed on Apr. 10, 1998.

(51) Int. Cl.[7] ................................................. G06G 7/48
(52) U.S. Cl. ..................... 703/6; 703/2; 703/5; 702/39; 356/432
(58) Field of Search ................................ 703/1, 2, 6, 5; 702/39, 33, 136, 138; 356/492, 432; 372/92, 93, 94

(56) References Cited

U.S. PATENT DOCUMENTS

| | | | | |
|---|---|---|---|---|
| 5,485,843 A | * | 1/1996 | Greenstein et al. | 600/455 |
| 5,604,592 A | * | 2/1997 | Kotidis et al. | 356/493 |
| 5,638,396 A | * | 6/1997 | Klimek | 372/92 |
| 5,724,138 A | * | 3/1998 | Reich et al. | 356/492 |
| 6,198,538 B1 | * | 3/2001 | Klimek et al. | 356/432 |

OTHER PUBLICATIONS

Spies et al., "Transducer Bean Field Modeling in Anisotropic Medi by Sup erposition of Gaussian Base Functions", Proc. IEEE Untrasonics Symposium, vol. 1pp. 685–688, Nov. 1996.*

Hsu et al., "A Point Source/Point Receiver Method for Ultrasonic Testing", Proc. IEEE Ultrasonics Symposium, vol. 1, pp. 291–295, Nov. 1993.*

(List continued on next page.)

Primary Examiner—Russell W. Frejd
(74) Attorney, Agent, or Firm—Mills & Onello LLP

(57) ABSTRACT

In an apparatus and method for remote ultrasonic determination of thin material properties using signal correlation, a method and apparatus are provided by which an arbitrarily-oriented anisotropic thin material may be interrogated for characterizing an unknown material property value thereof. The unknown material property may comprise for example temperature, pressure, elastic constants, density, hardness, composition, crystal orientation, grain size, and residual stress, or any material property that is variable with respect to known physical parameters of the material, for example known material elastic constants and/or density. In a first embodiment, theoretical signals are generated, for example a theoretical signal matrix, to characterize a material property value of a thin anisotropic material. A model of the thin material is generated comprising the behavior of the known material physical properties as functions of the unknown material property value to be characterized. For a plurality of known material thicknesses and known material property values, a transduction mechanism is simulated at a source location for generating a simulated elastic stress wave operating on the model at a plurality of source locations. The simulated intensities of signals generated by the simulated elastic stress waves are computed at a sense location to provide a representative composite signal. Theoretical signals are determined from the composite signal at each thickness and at each material property value. In a second aspect, the present invention is directed to a method for empirical characterization of a transduction event in a thin material using iterative temporal decomposition of an initial estimate of the transduction event converging on a measured signal.

48 Claims, 13 Drawing Sheets

P. Kotidis and D. Klimek "Industrial Demonstrations of Laser–Ultrasonics Based Process Control, Utilizing the Textron Laserwave™ Analyzer" *Nondestructive Characterization of Material VIII,* Robert E. Green Jr., (Plenum Press, New York, 1988), p. 341–346.

Y.J. Lee, B.T. Khuri–Yakub, and K.C. Saraswat, "Temperature measurement in rapid thermal processing using acoustic techniques", *Rev. Sci. Instrum.* 65(4). Apr. 1994, P. 974–976.

Yichi Lu, Mary V. Moore, Doug T. Queheillalt, and Haydn N.G. Wadley, "A Lamb Wave Temperature Sensor for Semiconductor Wafer Processing", *Review of Progress in Quantitative Nondestructive Evaluation,* vol. 13, D.O. Thompson and D.E. Chimneti, (Plenum Press, New York., 1994.) P. 509–516.

P. Cielo, F. Nadeau, and M. Lamontagne, "Laser generation of convergent acoustic waves for material inspection", *Ultrasonics,* Mar. 1985. (Butterworth & Co, 1985) P. 55–61.

Y. Li and R. B. Thompson, "Propagation of Guided Elastic Waves in Orthotropic Plates" *Journal of Applied Mechanics,* (1989) p. 189–196.

Adnan H. Nayfeh and D.E. Chimenti, "Free Wave Propagation in Plates of General Anisotropic Media" *Journal of Applied Mechanics.* (1989) p. 181–188.

R.L. Bratton, S.k Datta, and A.H. Shah, "Anisotropy Effects on Lamb Waves in Composite Plates", QNDE (1989) p. 197–204.

W.P. Rogers, "Elastic Property Measurement Using Rayleigh–Lamb Waves" *Res Nondestr Eval* (1995) 6:185–208, Springer–Verlag New York Inc.

Harry I. Ringermacher and Andrew D.W. Mckie, "Laser Ultrasonics for the Evaluation of Composites and Coatings" Materials Evaluation (Dec. 1995) p. 1356–1361.

Dan Klimek, Brian Anthony, Agostino Abbate and Petros Kotidis, "Laser Ultrasonic Instrumentation for Accurate Temperature Measurement of Silicon Wafers in Rapid Thermal Processing Systems". Mat. Res. Symp. Proc. vol 525, 1998 Material Research Society, p. 135–140.

John H. Mcleod, "The Axion: A New Type of Optical Element", *Journal of the Optical Society of America,* vol. 44, No. 8, Aug. 1954, p. 592–597.

Pierre–Andre Belanger and Marc Rioux, "Ring pattern of a lens–axicon doublet illuminated by a Gaussian–beam", *Applied Optics,* vol. 17, No.7, Apr. 1978, p. 1080–1086.

M.Rioux, R. Tremblay, and P.A. Belanger, "Linear, annular, and radial focusing with axicons and applications to laser machining" *Applied Optics,* vol 17, No. 10, May 1978, p. 1532–1536.

H.I. Ringermacher, F.A. Reed and J.R. Strife, "Laser Ultrasonics for Coating Thickness Evaluation at 1200° C", *Review of Progress in Quantitative Nondestructive Evaluation,* vol. 12, (1993) p. 549–558.

Michael J.S. Lowe, "Matrix Techniques for Modeling Ultrsonic Waves in Multilayered Media", *ieee Transactions on Ultrasonics, Ferroelectrics, and Frequency Control,* vol. 42, No. 4, Jul. 1995, p. 525–542.

Aleksander Pilarski and Joseph L. Rose, "Lamb Wave Mode Selection Concepts for Interfacial Weakness Analysis", *Journal of Nondestructive Evaluation,* vol.11, Nos. 3/4, 1992, p. 237–249.

S.A. Markus, M.D. Kaplan, and S.V. Veremeenku, "Propagation of Natural Waves in Orthotropic Plates", *Acoustic Methods,* vol. 21: 739–744, Plenum Publishing Corporation, (1986).

M.J. S. Lowe and P. Cawley, "The Applicability of Plate Wave Techniques for the Inspection of Adhesive and Diffusion Bonded Joints", *Journal of Nondestructive Evaluation,* vol. 13, No. 4, 1994, p. 185–200.

* cited by examiner

APPARATUS AND METHOD FOR REMOTE ULTRASONIC DETERMINATION OF THIN MATERIAL PROPERTIES USING SIGNAL CORRELATION

RELATED APPLICATIONS

This application claims the benefit of U.S. Provisional Application No. 60/081,312, filed Apr. 10, 1998, the contents of which are incorporated herein by reference in their entirety.

BACKGROUND OF THE INVENTION

Non-destructive testing of thin anisotropic materials using plane wave excitation and detection has been studied extensively. In recent years, an interest has emerged in the development of dispersion curve inversion and group velocity inversion procedures. The general approach in many of these procedures is to align the excitation event, also referred to as the "transduction mechanism," and detection location, along the known crystal axis, and to analyze the detected signal to determine elastic constants, bond quality, thickness, or any of a number of additional parameters. Unfortunately, many of these techniques fail to perform adequately when the target's crystal axis is rotating with respect to the excitation axis, or when the coordinate form of the crystal axis is unknown.

SUMMARY OF THE INVENTION

The present invention is directed to a method and apparatus by which an arbitrarily-oriented anisotropic thin material may be interrogated for characterizing an unknown material property value thereof The material property may comprise, for example, temperature, hardness, elastic constants, composition, crystal orientation, grain size, pressure, and residual stress, or any material property that is variable with respect to known material physical parameters.

For purposes of the present invention, the known material physical parameters may comprise a subset of the unknown material property values. To distinguish them, the unknown material property values to be characterized are referred to herein as "material property values," while the known material property values are referred to herein as "material physical parameters."

In a first embodiment, the method of the present invention is directed to a method for generating theoretical functions to characterize an unknown material property value of a thin anisotropic material. First, a model of the thin material is generated. The model preferably comprises the behavior of known material physical parameters, for example elastic constants and material density, as functions of the material property value to be characterized, for example temperature. For a plurality of known material thicknesses and known material property values, a transduction mechanism is simulated at a source location for generating a simulated elastic stress wave operating on the model at a plurality of source locations. The simulated intensities of signals generated by the simulated elastic stress waves are computed at a sense location to provide a representative composite signal. Theoretical functions, for example a matrix of equivalent modal excitation functions, are determined for symmetric modes and anti-symmetric modes from the composite signal at each thickness and at each material property value.

In a preferred embodiment, following determination of the theoretical functions, an elastic stress wave is generated in a material of unknown thickness and unknown material property value at a source location. The intensity of a measured signal generated by the elastic stress wave is sensed at a sense location positioned a known distance from the source location. The measured signal is correlated to the theoretical functions to determine correlation values. The material thickness value and material property value are determined based on the best correlation values.

In a preferred embodiment, the step of correlating comprises pattern recognition, or alternatively a variation of in-step correlation. The transduction mechanism may comprise a simulation of ring excitation comprising a plurality of line excitations arranged tangentially about a ring. The material property preferably comprises a property selected from the group consisting of temperature, pressure, elastic constants, density, hardness, composition, crystal orientation, grain size, and residual stress.

In a second aspect, the present invention is directed to a method for empirical characterization of a transduction event in a material. A transduction event is initiated in a material to generate a measured signal. An initial estimate of the transduction event is propagated along known dispersion curves characterizing the material to generate a theoretical signal. The measured and theoretical signals are decomposed and their respective amplitudes are determined along the dispersion curves. In a preferred embodiment, the average amplitudes are determined. The decomposed measured and theoretical signals are compared to generate an error signal. The error signal, in turn, is used to modify the initial estimate.

In a preferred embodiment, the steps of propagating, decomposing, comparing, and modifying are performed iteratively until the error signal is within acceptable limits. The theoretical signal is preferably time-shifted with respected to the measured signal such that they are substantially contemporaneous in time. The characterized transduction event is preferably of the form of a modal excitation function. The material is preferably a thin anisotropic material which may be of unknown thickness. The steps of propagating and temporal-decomposing are preferably performed along a plurality of unique orientations for the material. The step of temporal decomposing may comprise for example decomposing using the continuous wavelet transform, the short-time Fourier transform, the Wigner-Ville transform, and/or the Choi-Williams transform. The measured and theoretical signal may each comprise symmetric and anti-symmetric modes of propagation.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

The present invention is directed to a method and apparatus by which an arbitrarily-oriented anisotropic thin material target may be interrogated to determine any of a number of material properties in an efficient, cost effective, and accurate manner. The material property may include, for example, temperature, hardness, composition, crystal orientation, grain size, pressure, and residual stress. Where, for example, temperature is the material property to be determined, accuracy on the order of less than 1° C. at one standard deviation is attainable.

In a preferred embodiment, a model of the thin material comprising the behavior of the known thin material physical parameters as functions of the unknown material property value to be characterized is generated. The model may comprise, for example, a model of the known behavior of elastic constants and material density as functions of temperature for the material. Such properties are well characterized for silicon, for example. The material properties, along with the thickness and free-boundary conditions, determine the propagation physics of the material. The propagation physics in turn define the manner in which a pulse of energy, or transductance event, travels along the thin guiding layer. An initial disturbance is propagated along the material, the behavior of which is a function of propagation physics, as well as the distance between the event source and the detection location. Once theoretical signals, or model excitation signals are calculated, they are stored, for example in the form of a matrix, and a received experimental signal is correlated with the matrix of theoretical signals. The correlation result indicates the unknown material property values, for example temperature and thickness, of the thin material under test.

Figure 1:
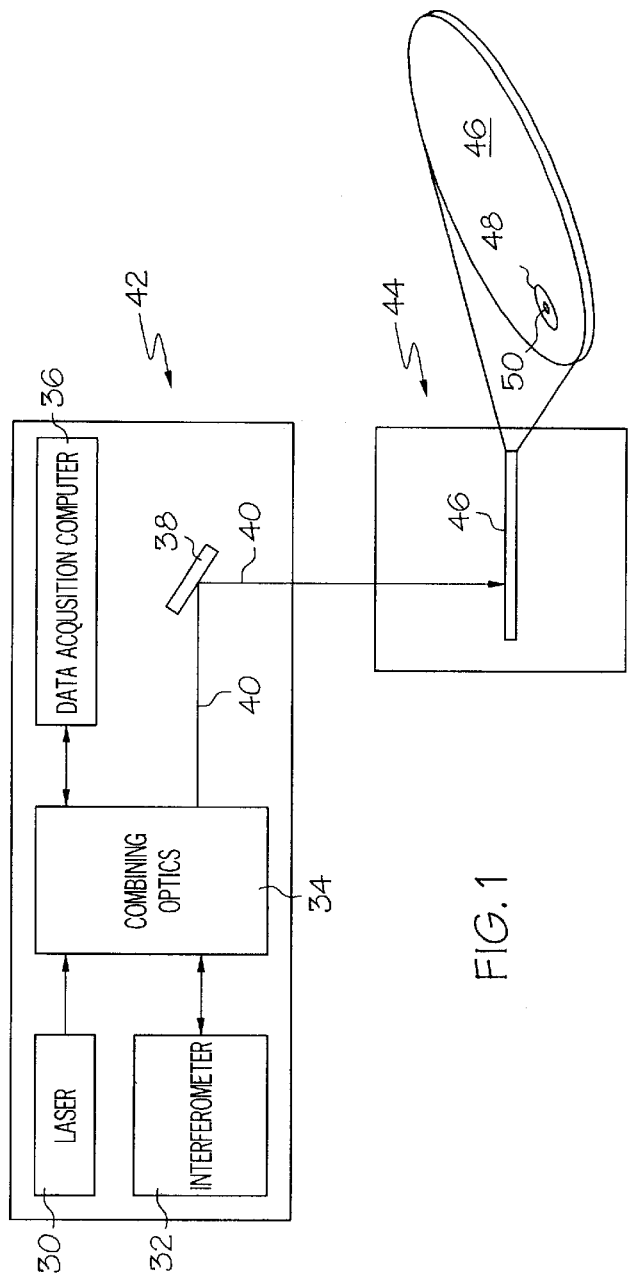
FIG. 1 is a schematic block diagram of the primary components of the system of the present invention.

FIG. 1 is a schematic block diagram of the primary components of a preferred embodiment of the present invention. The temperature monitoring system 42 comprises a laser 30, for example an impulse laser, a polarizing interferometer 32, combining optics 34, and a computer 36 for acquiring and processing data. In a preferred embodiment, calibration computations are performed by computer 36. The optics 34 generate a laser beam 40 which is directed by directing optics 38 into a processing oven 44 where silicon wafers 46 are processed. When the output beam 40 strikes the wafer 46, ultrasonic waves are generated in the wafer material. For example, the laser may comprise a Nd:YAG laser (532 nm wavelength) pumped by a flashlamp and doubled with a doubling crystal having a 10 nsec pulse energy, operating at 10 pulses per second. Pulse energy is preferably on the order of 20 mJ per pulse.

The ultrasound signal is detected using a polarizing interferometer 32, for example a polarizing interferometer equipped with a diode-pumped continuous wave Nd:YAG probe laser of wavelength 1064 nm. The two laser beams, source beam and sense beam, are prepared and combined into a coaxial configuration and directed to the sample 46. Reflected probe laser power returns to the interferometer combined with an inertial reference beam, and is sent to a photodiode detector. The intensity signal from this detector portrays the surface displacement caused by the ultrasound wave created by the impulse laser. The signal is sent to the data acquisition computer 36 where the information is processed.

In a preferred embodiment, the well-characterized technique of ring excitation is employed. The purpose of the combining optics 34 in this embodiment is to modify the impulse laser beams output from laser 30 so that when the resulting output beam 40 is focused on the silicon wafer 46, the beam 40 is in the form of a sharp ring 48. An axicon is used for this purpose. In this manner, the output beam 40 launches an elastic stress wave, which generates an ultrasound signal converging toward the detection probe point 50 located in the center of the ring. This arrangement confers several advantages over other well-known excitation techniques, including point excitation and line excitation. Advantages include improved signal-to-noise ratio, and a minimal amount of laser energy deposited on the wafer 46. A preferred ring 48 diameter is 2.54 cm. This diameter is considered an optimal tradeoff between the requirement for temporal feature resolution and the need to localize the interrogation zone. Smaller and larger measurement areas are equally applicable to the present invention.

In general, laser energy absorbed on the surface of the material generates several types of ultrasonic waves; some of them penetrate into the material, while others propagate along the surface. The surface waves involve a displacement transverse to the direction of motion. These waves, referred to as Rayleigh waves, are generated when the material is much thicker than the ultrasound wavelength.

When thin materials, or plates, are excited, both the upper and lower surfaces of the material become involved in wave generation and waves referred to as Lamb waves result. Lamb waves have a strong dispersive behavior. There are two basic modes of Lamb waves, symmetric and anti-symmetric. Illustration of the zeroth order form of these modes are given in FIG. 2. The behavior of these modes is well characterized and understood by those skilled in the art.

For purposes of the present invention, the term "thin material" or "thin wafer", as used herein, is defined as a material which is sufficiently thin, such that when the material is excited by a transduction event, Lamb waves are generated in the material, as opposed to Rayleigh waves.

Figure 2:
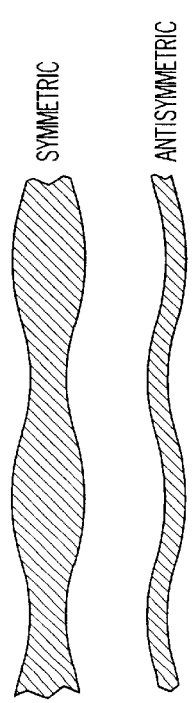
FIG. 2 is an illustration of symmetric and anti-symmetric Lamb modes in accordance with the present invention.

The laser induces an ultrasound pulse in the wafer 46 that includes many frequencies. Ultrasound propagation through thin plates is characterized by means of Lamb modes. Lamb modes cause complex interactions between longitudinal and shear displacement waves reflecting between the surfaces of the plate. As illustrated in FIG. 2, Lamb modes can be characterized as either symmetric or anti-symmetric, referring to the symmetry of transverse displacements of the material relative to a plane parallel to and halfway between the two surfaces. Lamb modes are multi-modes in the sense that they include zeroth order and higher order modes. Because of the dispersive nature of Lamb waves and the characteristics of the anti-symmetric mode, the signal is distributed with respect to time; high-frequency waves arrive at the interrogation point 48 earlier than low-frequency waves. The relationship between frequency and velocity is complex and depends on the type and order of the mode involved. In a laser ultrasound apparatus, the duration of the impulse laser is short, on the order of 10 nsec, and the focal dimensions can be small, on the order of 50–200 microns. The consequence of this impulse excitation is that many frequencies are excited. This, coupled with the dispersive nature of plate mode propagation, results in a complex signal shape.

Figure 3:
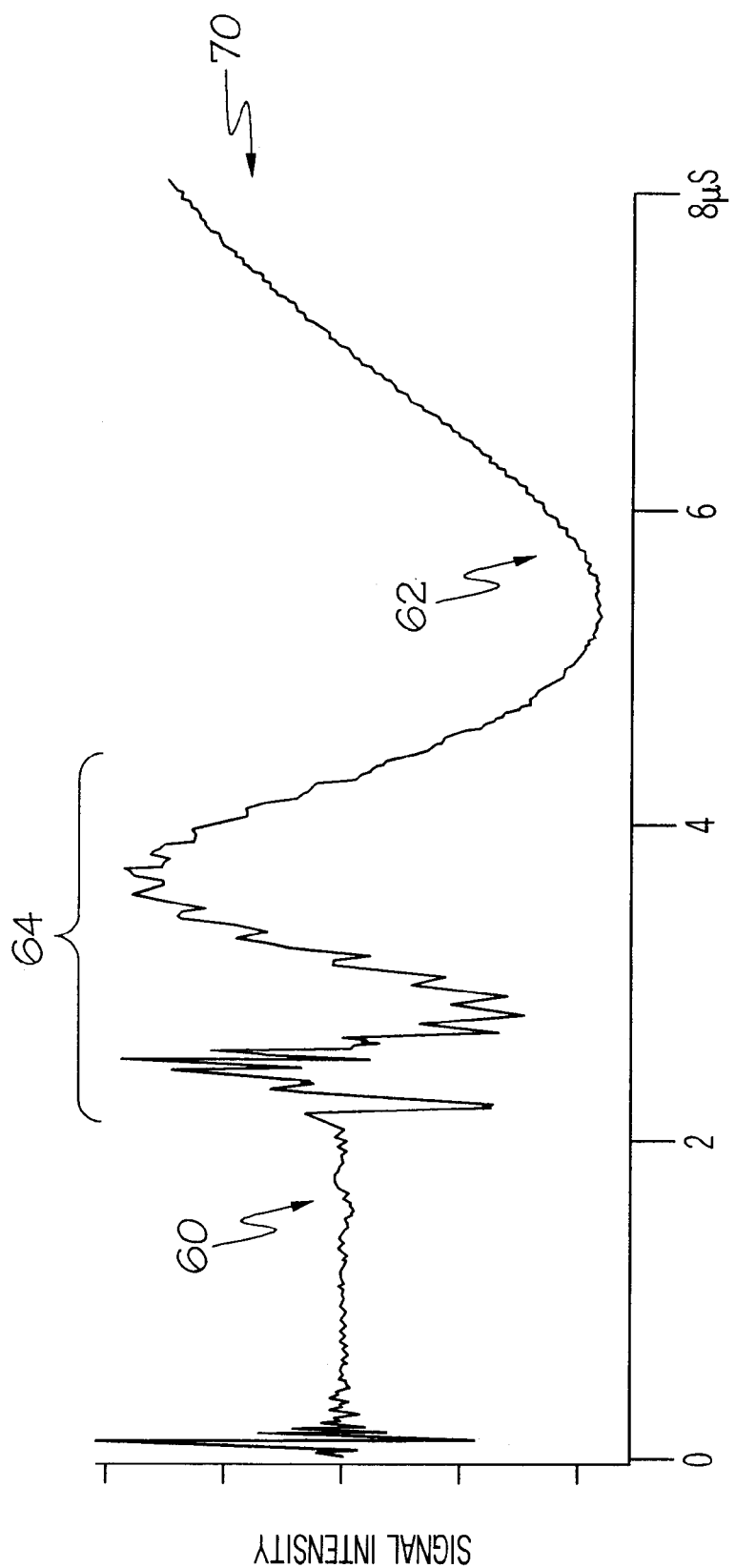
FIG. 3 is a chart of signal intensity as a function of time for a typical detected signal in accordance with the present invention.

A typical laser ultrasound signal shape 70 generated by axicon-formed ring excitation is shown in FIG. 3, which is a chart of signal intensity as a function of time. At time 0 $\mu$s, a transduction event takes place, introducing an elastic stress wave in the material along the perimeter of the ring 48. A sensor, for example a sense beam 50 positioned at the center of the ring 48 receives a first displacement signal 60 which is observed at approximately 1.4 $\mu$s. This is indicative of the arrival of the lowest order symmetric mode. The low-frequency modulation 62 continuing beyond a time of 6 $\mu$s is the lowest order anti-symmetric mode. The signal portion 64 ranging from 1.4 to 5 $\mu$s is a function of a combination of higher-order symmetric and anti-symmetric modes.

The velocity of ultrasound varies considerably as a function of angle through the cubic crystal structure of the material, for example silicon. Longitudinal velocity varies by about 10% and shear velocity varies by about 25%. This, coupled with the fact that ring excitation is preferred, means that the signal pattern observed is a sum of many such patterns for each angle of propagation from the ring 48 to the central detection point 50. Although, from a conceptional point of view, it may be preferred to employ simple and well-characterized signals, this simplicity is outweighed by the advantages of ring excitation, which produces the best possible signal-to-noise ratio. High signal-to-noise ratio is necessary because of the accuracy and precision to which the signal features are measured. The converging Lamb wave created by the ring provides a signal of sufficient quality. Modern RTP furnaces employ a rotating wafer configuration. Ring excitation is well suited for such a configuration. Because of the level of accuracy required, it is difficult to determine the precise angle of the wafer that was present during measurement. By averaging over all angles, the resulting signal has minimal dependence on wafer orientation. Any residual dependence due to non-uniformity of the ring is removed by averaging over several measurements taken as the wafer is rotated through 90 degrees. Furthermore, using only a single angle would restrict the rate at which one could accumulate the number of signals comprising the average signal used to evaluate temperature. With single angle measurements, signals can only be obtained once every 90 degrees of rotation.

As stated above, Lamb modes are made up of complex interactions between longitudinal and shear displacement waves reflecting between the surfaces of the plate. Since both surfaces are involved, the separation between the surfaces or wafer thickness, strongly influences their character. The group velocity dispersion curves, which describe the change in velocity for each mode as a function of frequency, are actually a function of the frequency time thickness product. Although average wafer thickness in any given batch of wafers is known, variation in the thickness may be on the order of 1–2%. Since the pattern of the signal is strongly influenced by thickness, the methods of temperature evaluation must take this in to account.

It is well-known that the elastic properties of silicon vary slightly with temperature. In other words, there is a very subtle change in the propagation velocity of a signal through the silicon as a function of temperature. For example, in a standard silicon wafer, the velocity of propagation may change by a factor of $3.2\times10^{-5}$ per $°$ C. Assuming that this degree of accuracy is required, this is a challenging task when considering that any jitter, or variation in the source beam or sense beam will result in a large amount of jitter in the velocity measurement. For example, a jitter in distance of 0.78 micron results in a jitter in temperature measurement of 1° C. Furthermore, accuracy in time is also needed. As an example, a 0.16 nsec time jitter results in jitter in temperature measurement of 1° C. Since the silicon wafer is to be measured at a sensitivity of $3.2\times10^{-5°}$ C.$^{-1}$, accurate temperature measurement is a challenging task.

Figure 4:
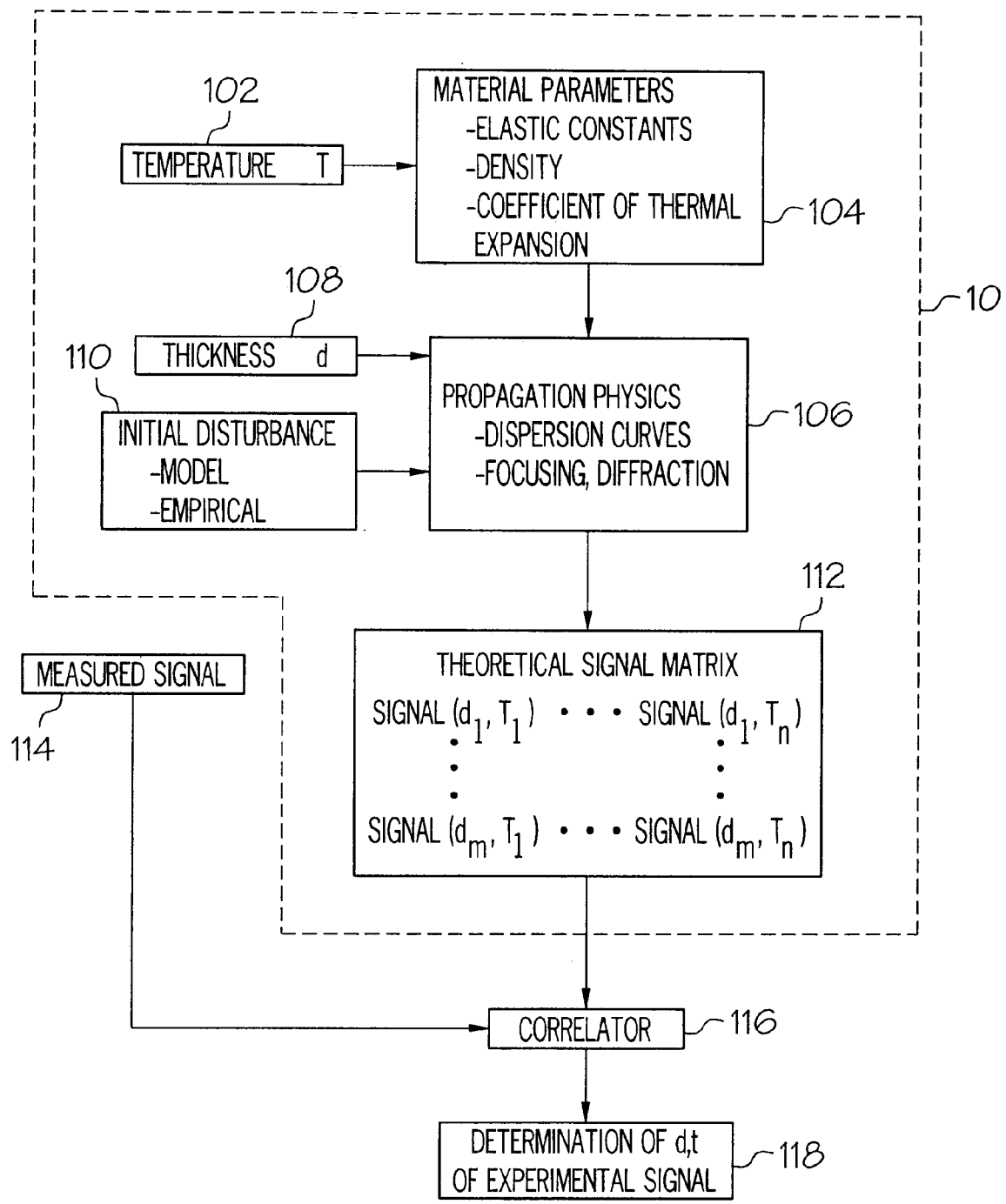
FIG. 4 is a flow diagram illustrating the steps involved for extracting a material value, for example temperature and material thickness, from measured transductance event signals in accordance with the present invention.

As stated above, the present invention is directed to a method and apparatus by which an arbitrarily-oriented anisotropic thin target may be interrogated and by which material property values thereof may be determined. FIG. 4 is a flow diagram of a technique for extracting an unknown material parameter, for example, temperature, as well as thickness, based on measured signals in accordance with the present invention.

In a first step 101, model signals for the material under test are calculated in the form of a theoretical signal matrix 112. In general, the material parameters 104 of a given thin material are well defined. For example, in the case of silicon, elastic constants and density are well-known functions of temperature, and have been studied extensively. The material properties 104, along with material thickness 108 and boundary conditions, for example, as generated by an initial disturbance 110, determine the propagation physics 106 of the material. The propagation physics define the manner in which a pulse of energy will travel along the thin material. An initial disturbance 110, whether determined in a model or empirically, propagates according to the propagation physics 106 along the material between the source location of the transduction mechanism and the sense location. Such propagation 106 is used to generate a matrix 112 of theoretical functions that vary with respect to the material property, for example, thickness d and temperature T. The theoretical signal matrix 112 may be pregenerated in an experimental apparatus, or, alternatively, computed in real time, depending on the availability of adequate computer resources.

Upon generation of the theoretical signal matrix 112, the matrix 112 can be applied to a correlator 116. The correlator 116 may comprise, for example, a match filter correlator as described in U.S. patent application Ser. No. 09/289,569, now U.S. Pat. No. 6,198,538. "Match Filter Apparatus and Method for Remote Ultrasonic Determination of Thin Material Properties," by Daniel E. Klimek and Petros A. Kotidis, filed of even date herewith and commonly owned with the present application, incorporated herein by reference. Measured signals 114 captured using a material under test are generated and correlated with the theoretical signal matrix 112 at correlator 116. The correlation result, for example, the maximum correlation, determines the value of the material properties for the material under test, for example temperature and thickness.

For an isotropic material, it is relatively simple to demonstrate the equivalence in shape between first, a propagating signal generated at a ring source of radius R and converging on a transducer at the center of the ring, and second, a line source generating a plane wave detected by a transducer located at a normal distance R from the source.

However, assuming an anisotropic medium, a plane wave generated by a transductance event, propagating along a particular direction, is different from all other directions. This is because the dispersion relationships, and the physics of propagation are highly dependent on the direction of propagation for an anisotropic material. Therefore, in an anisotropic medium, a plane wave propagating along any one direction, and a circularly-converging wave, no longer produce the same results.

Figure 5:
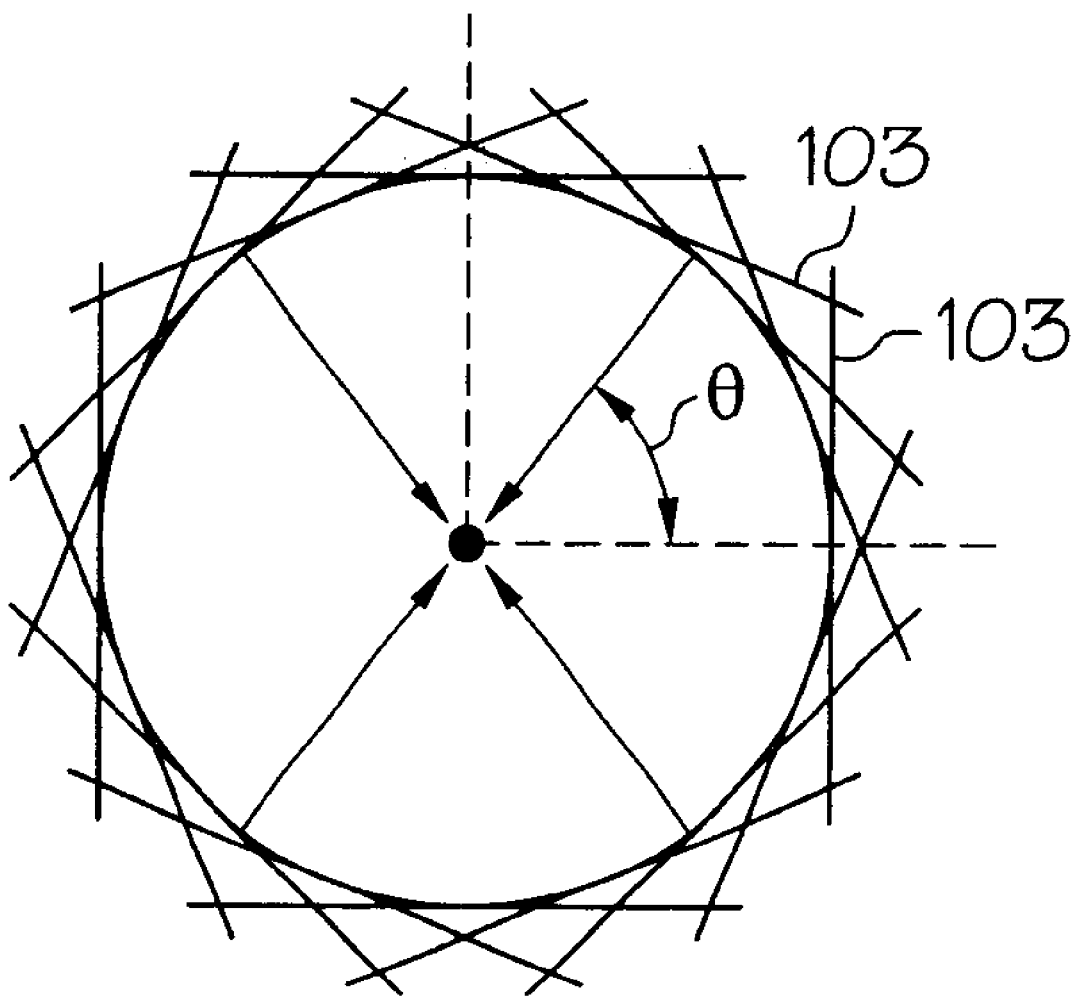
FIG. 5 is a schematic model of an approximation for excitation of Lamb waves generated about the circumference of a ring in accordance with a preferred embodiment of the present invention.

An initial step in the inventive system and process illustrated in FIG. 4 is the generation of a model for characterizing the initial disturbance 110. For purposes of the present invention, a model utilizing the summation of plane waves for each mode generated along lines 103 tangentially oriented about the circumference of a ring as illustrated in FIG. 5 will be employed. Other models are possible. For example, a semicircle or arcuate transduction event. This model is represented by the following relationship:

$$\text{Signal}(x_o = \text{center}, t) = \sum_{Modes} \left\{ \sum_{\Theta=0}^{45} \left[ \sum_{k=-\infty}^{\infty} A_o(\text{Mode}, k, \Theta) e^{-j(k \cdot x_o - w(\text{Mode},k,\Theta) \cdot t)} \Delta k \right] \Delta \Theta \right\} \quad (1)$$

where $w(\text{Mode},k,\Theta)$ represents the dispersion curves as a function of Mode and angle of propagation $\Theta$, $A_o(\text{Mode},k,\Theta)$ represents the spatially-distributed, temporally-impulsive initial disturbances for all modes at all angles, and wherein the quantity within the square brackets [ ] corresponds to the inverse Fourier representation of a single plane wave.

While the above-described model does not include certain optical anomalies, for example refraction, focusing, and associated non-linearities, such effects do not play a major role at desired accuracies in contemporary systems. However, the model may be enhanced to take such optical inconsistencies into consideration.

Figure 6B:
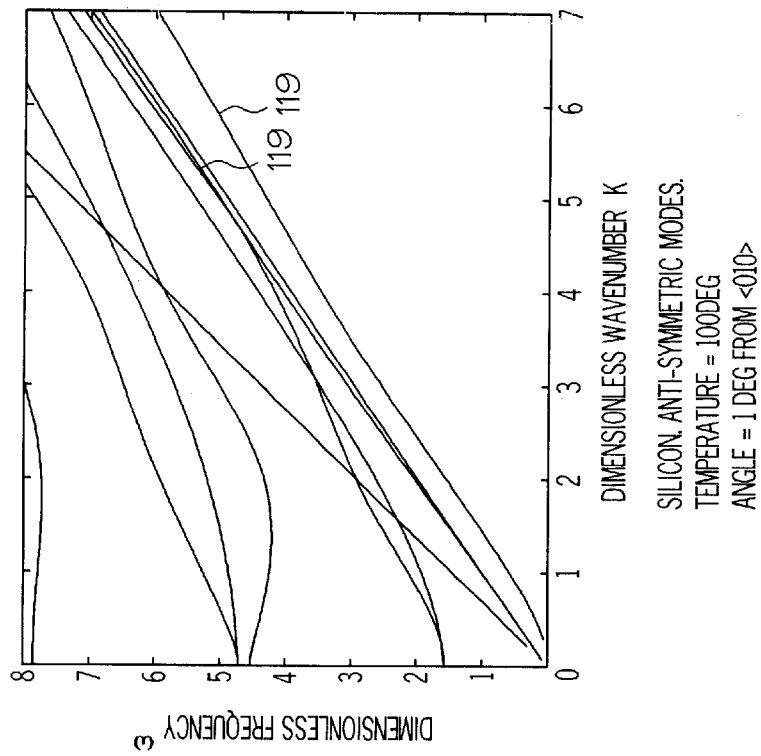
FIGS. 6A and 6B illustrate the variance in dispersion characteristics for a small change in propagation angle, for example one degree, for an anisotropic medium in accordance with the present invention.
Figure 6A:
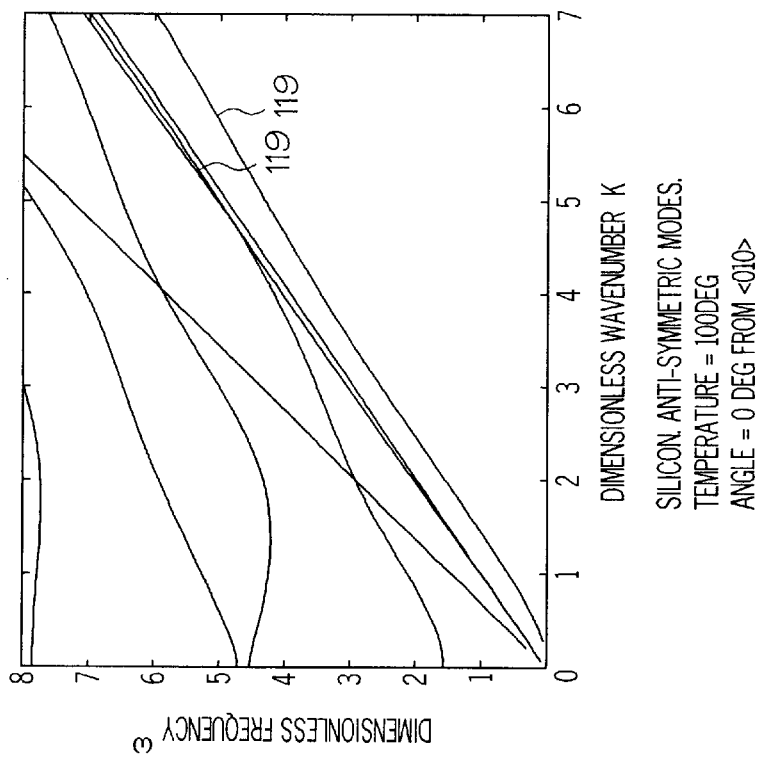

The dispersion curves $w(\text{Mode},k,\Theta)$ of the model are also highly dependent on propagation angle as illustrated in FIGS. 6A and 6B which illustrate anti-symmetric modes for silicon at a temperature of 100 C. at angles of 0° and 1° from the primary axis <010>. Each plotted line 119 on the chart represents a mode, and it can be seen that as the angle varies, new modes appear and disappear, and the characteristics of a given mode may vary.

Figure 7B:
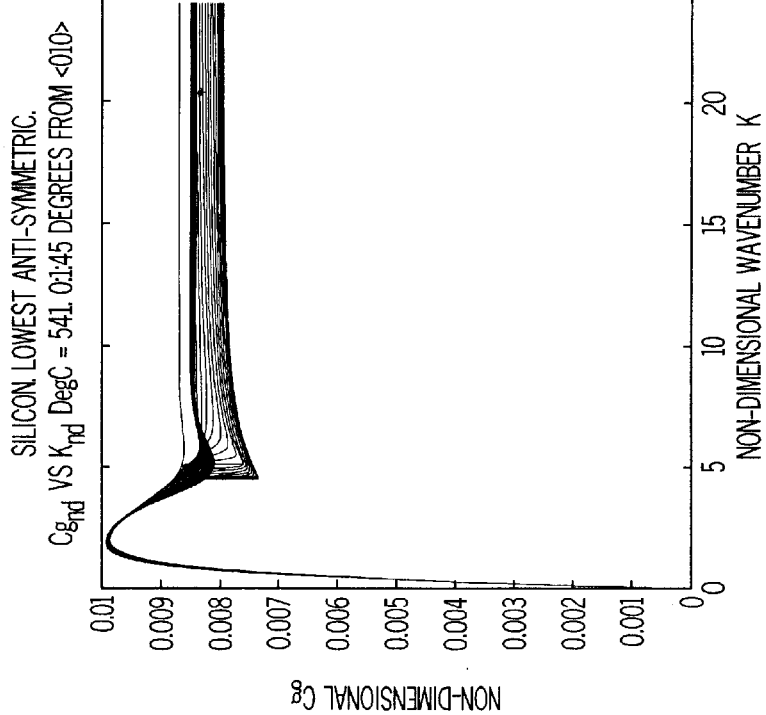
FIGS. 7A and 7B illustrate the variance in the dispersion curves for an anisotropic medium as a function of propagation angle for symmetric and anti-symmetric modes, respectively, in accordance with the present invention.
Figure 7A:
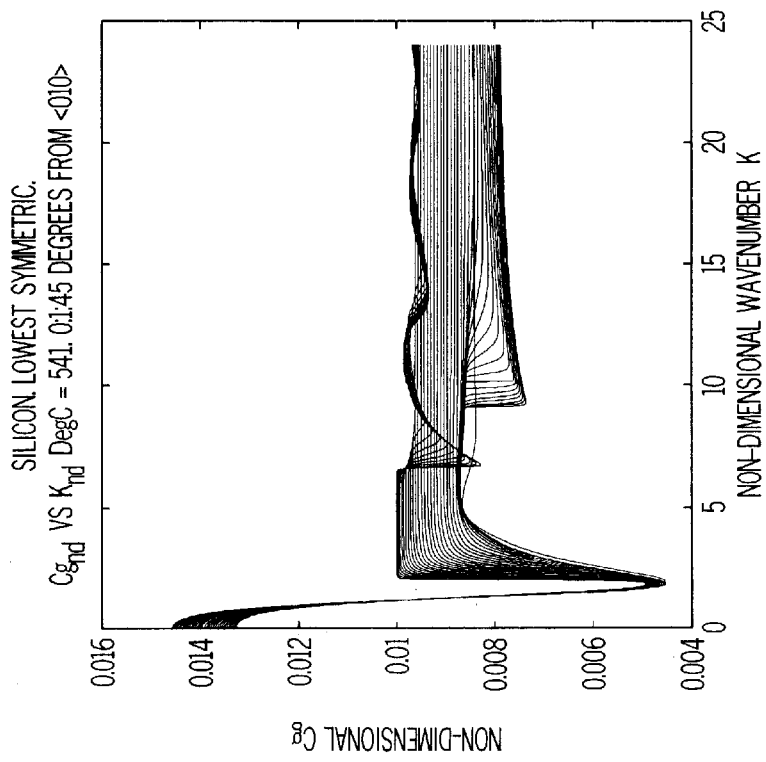

This variance is also exhibited in the dispersion curves of FIGS. 7A and 7B for the lowest order symmetric and anti-symmetric modes, respectively. These dispersion curves are determined by numerically computing the determinate of the equations of motion that arise from stress-free boundary conditions. The charts of FIGS. 7A and 7B illustrate the lowest order of symmetric and anti-symmetric mode group velocities (the first derivative of the dispersion relationship as a function of spatial frequency) for silicon at all unique angles (between 1 and 45 degrees) in one degree intervals as a function of wave number k.

Determination of the initial disturbance $A_o(\text{Mode},k,\Theta)$ is a more sophisticated computation. As shown in FIG. 4, the initial disturbances 110 can be determined by both computer simulation model or empirically. While a simulation model might be attainable, characterization of the highly-variable initial disturbances can be quite sophisticated. For this reason, in a preferred embodiment, the present invention is further directed to a system and method for empirical determination of the initial disturbances. In this technique, a wafer of known thickness is held at a known temperature. Data are collected on this known system and used to determine the unknown initial disturbances $A_o(\text{Mode},k,\Theta)$.

There is no known direct inversion procedure or technique that can be used with axicon excitation and single-point detection to determine the effective initial disturbance for every mode at every angle. However, a direct inversion technique exists for plane waves generated by line excitation. First, data are collected at numerous spatially separated points along the path of propagation. Next, a two-dimensional Fourier transform is performed on the data. The result is a three-dimensional image of varying amplitude curves in the spatial/temporal frequency domain. The curves themselves represent the actual dispersive modes (temporal vs. spatial frequencies); the amplitude along the curves across the spatial frequency axis represents the empirically-determined initial disturbances. Similarly, the initial disturbances $A_o(\text{Mode},k,\Theta)$ can be approximated by using plane waves along a number of crystal directions, or angles, and at several distances. From this, a combination of frequency-time and Fourier decomposition can be used to empirically determine the initial disturbances $A_o(\text{Mode},k,\Theta)$ for every mode and angle.

Although this could be modeled, however, for the layers of interest, the group velocity curves for several modes are very close in frequency and time and so it is difficult to determine the manner in which energy is distributed amongst the multiple modes at the multiple angles. Additionally, the optics employed to generate a line are substantially different from the optics used to make an axicon ring, such that the results determined empirically for a line source would not be as accurate as desired for use in the axicon model. For this reason, empirical determination of the axicon-generated ring data is preferred to a model determination. Since a direct inversion is impractical, an iterative empirical procedure as described below is preferred.

Figure 8:
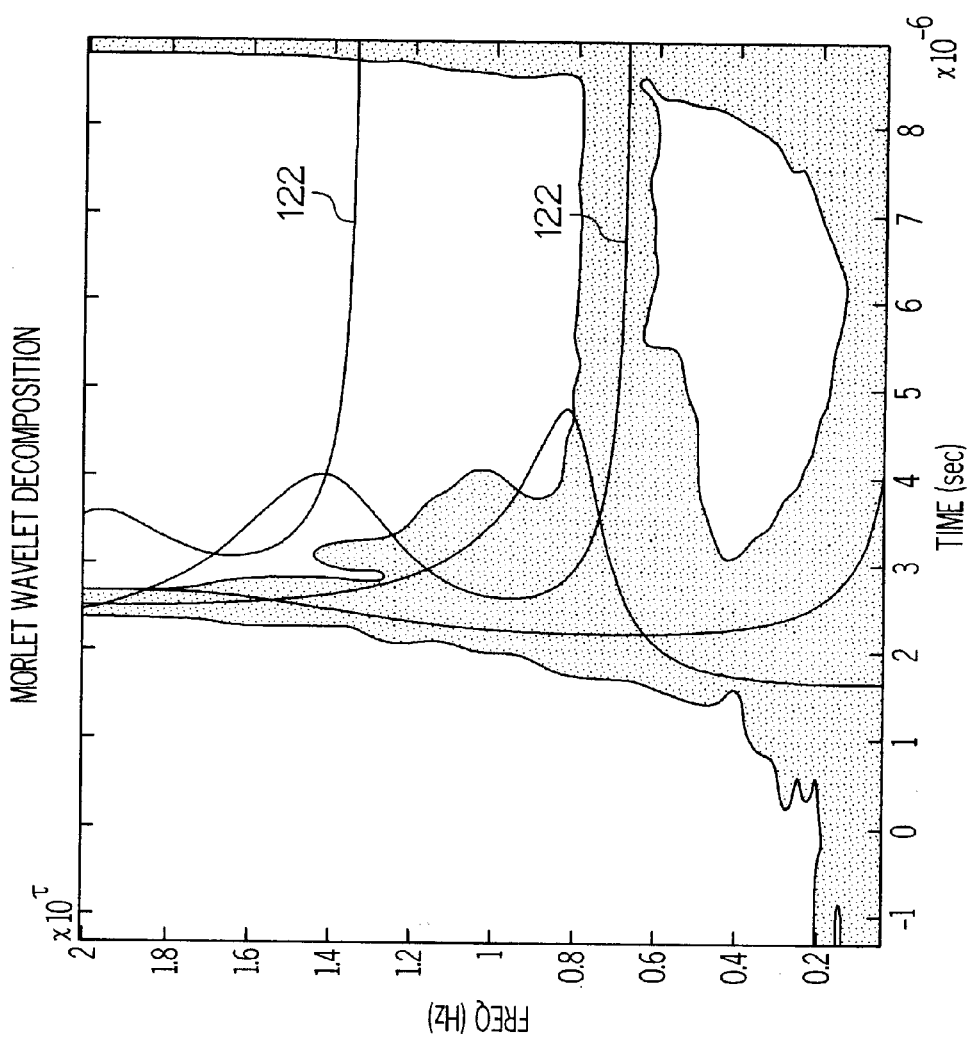
FIG. 8 illustrates a typical wavelet decomposition and dispersion curve along a single axis in accordance with the present invention.

FIG. 8 illustrates a temporal decomposition, for example a wavelet decomposition (frequency-time), of a plane wave signal as generated by a line source and detected at a single detection point. Theoretical group velocity curves 122 as shown in FIGS. 7A and 7B are overlaid. This experimental result demonstrates that a frequency-time decomposition of a signal can reveal the general form of the modes. The procedure to empirically determine the effective initial disturbances involves an iterative application of the temporal decomposition transform to real and theoretical signals. However, in the present application, the signal is axicon-generated and center-point detected. The axicon signal is constructed theoretically by a summation of all modes about the ring source for all directions of propagation as in Equation (1) above. With respect to FIG. 8, each, line 122 represents the term between the square brackets [ ] of Equation (1). It is evident that in the real signals of interest, only two axicon signals are present. These include the lowest-order anti-symmetric mode and the lowest-order symmetric mode.

To simplify the iterative procedure, in a preferred embodiment, an assumption is made that the effective initial disturbances are the same for all plane waves in each similar-mode signal. In this manner, the angle term $\Theta$ is removed from the initial disturbance $A_o(Mode,k,\Theta)$ computation. This assumption, together with the fact that only two similar-mode axicon-generated signals are present, simplifies the procedure such that only two spatial frequency distributions are to be determined.

Figure 9:
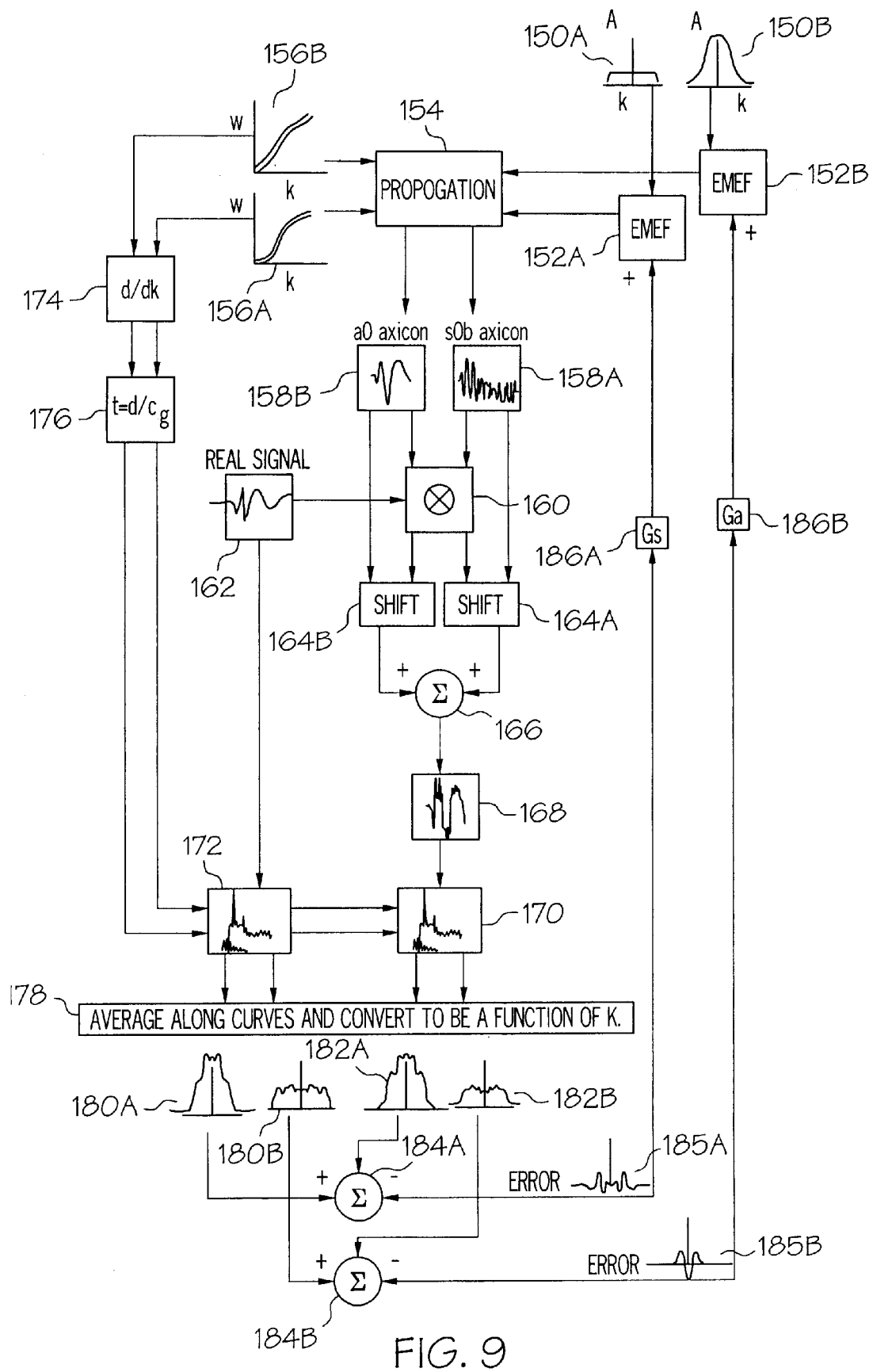
FIG. 9 is a flow diagram illustrating the use of wavelet decomposition in an iterative fashion to empirically determine theoretical excitation functions employed in the process and system of the present invention.

FIG. 9 is a flow diagram illustrating the empirical determination of the initial disturbances. First, an initial estimate is made for the symmetric initial disturbance 150A and the anti-symmetric initial disturbance 150B. The initial estimates 150A, 150B are applied to material propagation curves 156A, 156B (or dispersion curves of FIGS. 6A and 6B) at propagation unit 154 to generate theoretical symmetrical and anti-symmetrical axicon signals 158A, 158B respectively. A real signal is captured 162 and applied to combination unit 160 and utilized to determine the initial time shift for the theoretical signal. Based on this time shift determination, the symmetric and anti-symmetric axicons are shifted in time by shifters 164A, 164B, respectively, and combined at summation unit 166 to generate a theoretical signal 168. The amplitude of the temporal frequency-time decomposition along all modes of propagation is determined for both the theoretical signal 170 and the real signal 172, respectively. Next, the average amplitude of the two average dispersion curves 170, 172 are determined for the real and theoretical signals at unit 178. For the real signal 172, conversion units 174, 176 are used for the conversion of the dispersion curves from the w/k domain to the time/frequency domain. Following conversion of the averaged curves to be a function of wave number k, the difference between the anti-symmetric mode dispersion curve for the theoretical 182A and real 180A signals are calculated at difference unit 184A. Similarly, the difference for the real and theoretical anti-symmetric modes are determined at difference unit 184B. The difference represents the error between the initial estimate of the transduction mechanism 150A, 150B and the real transduction mechanism. The error signals are multiplied by a corresponding symmetric gain $G_s$ 186A, and antisymmetric gain $G_a$ 186B and applied to modify the initial estimates at summation units 152A, 152B. The gains 186A, 186B are computed depending on the relative balance of importance of the symmetric/ antisymmetric modes to the desired application.

As the initial approximation improves in accuracy, the iterative process converges much more rapidly. For example, assuming that the laser pulse serving as the excitation transducer is Lorentzian in cross-section, a Lorentzian-shaped initial approximation for the initial disturbance for the anti-symmetric modes is preferred. As the initial loading is almost completely orthogonal to the symmetric modes, it is postulated that the symmetric modes appear only via sympathetic and noise-type excitation from the anti-symmetric modes, and that no one frequency range in the symmetric modes would be more prevalent than any other. For this reason, a preferred initial approximation for this symmetric modes comprises a flat, white noise, distribution for the initial spatial frequencies.

Figure 10:
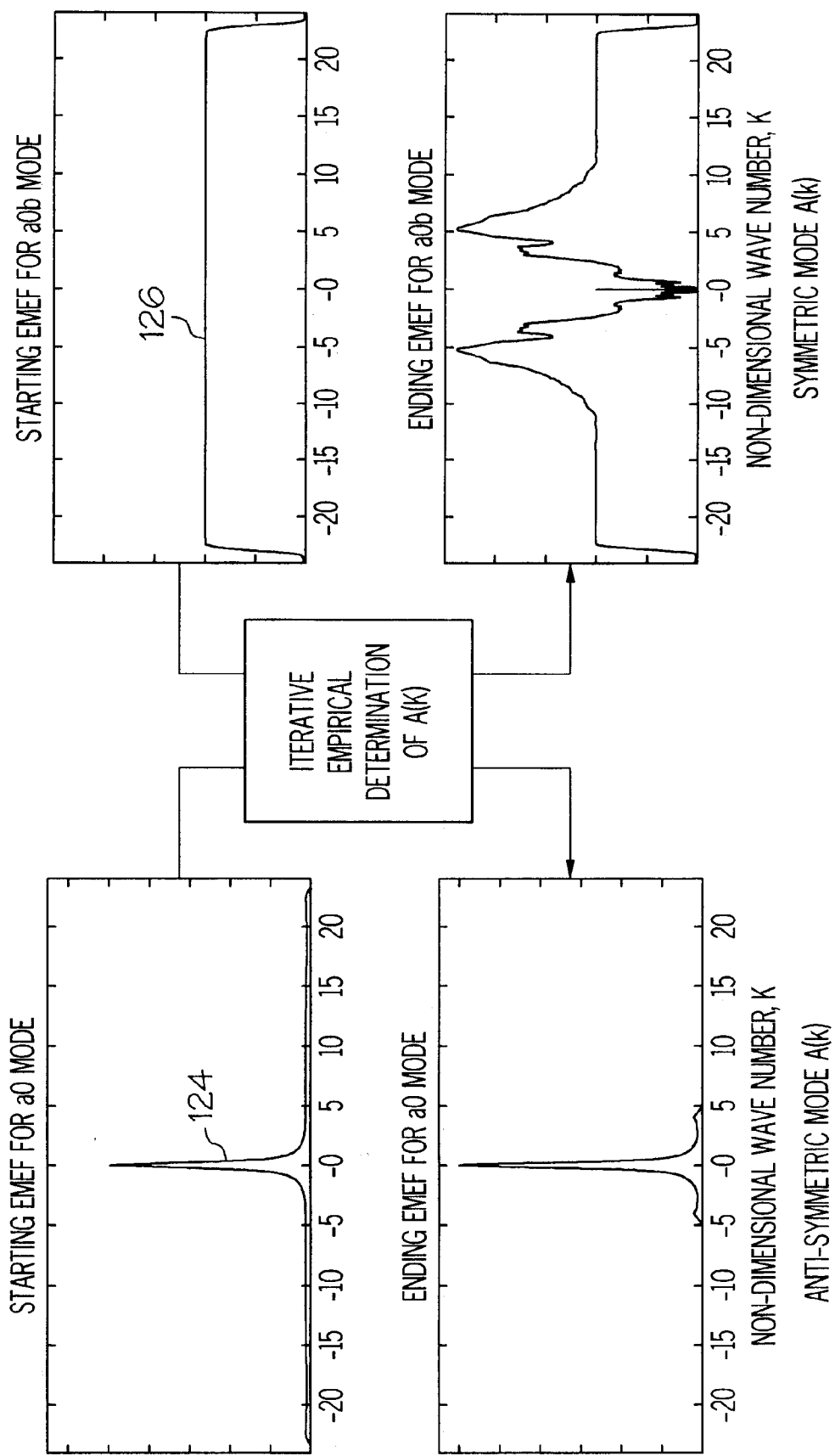
FIGS. 10A and 10B illustrate initial and final excitation functions determined by the process of FIG. 9.

FIGS. 10A and 10B are illustrative charts for the initial and final predictions of the initial disturbances for anti-symmetric and symmetric modes respectively. It can be seen that the initial estimate for the anti-symmetric mode 124 is Lorentzian in cross-section, while the initial approximation for the symmetric mode 126 is a white noise distribution. Other initial approximations are possible, depending on the system applications.

Figure 11:
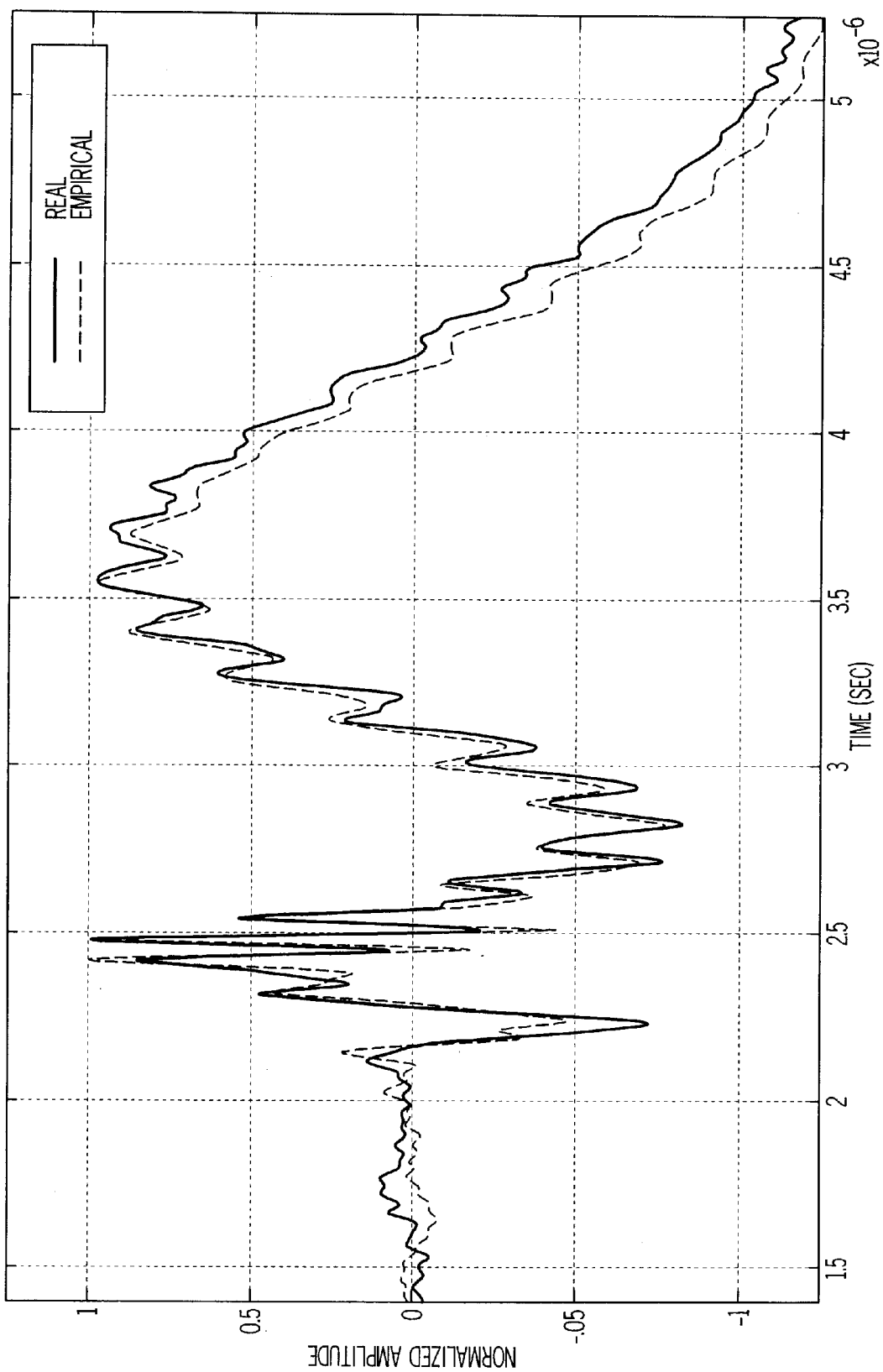
FIG. 11 illustrates the generated model signal in amplitude as a function of time as compared to the seed experimental signal in accordance with the present invention.

FIG. 11 is a plot of normalized amplitude as a function of time for the final, converged, empirically-determined theoretical signal, in comparison with the real measured signal 162 (see FIG. 9).

In a final step, the theoretically-determined dispersion curve 106 (see FIG. 4) and empirically-determined initial disturbances 110 are employed to calculate a matrix of theoretical signals 112 over a plurality of temperatures T and thicknesses d. Real signals, as measured by the test apparatus 114 are then matched at correlator 116, for example using pattern recognition techniques, with the matrix 112, to determine the unknown material property, for example temperature T, and the thickness d of the material under test as measured by signal 114.

Figure 12A:
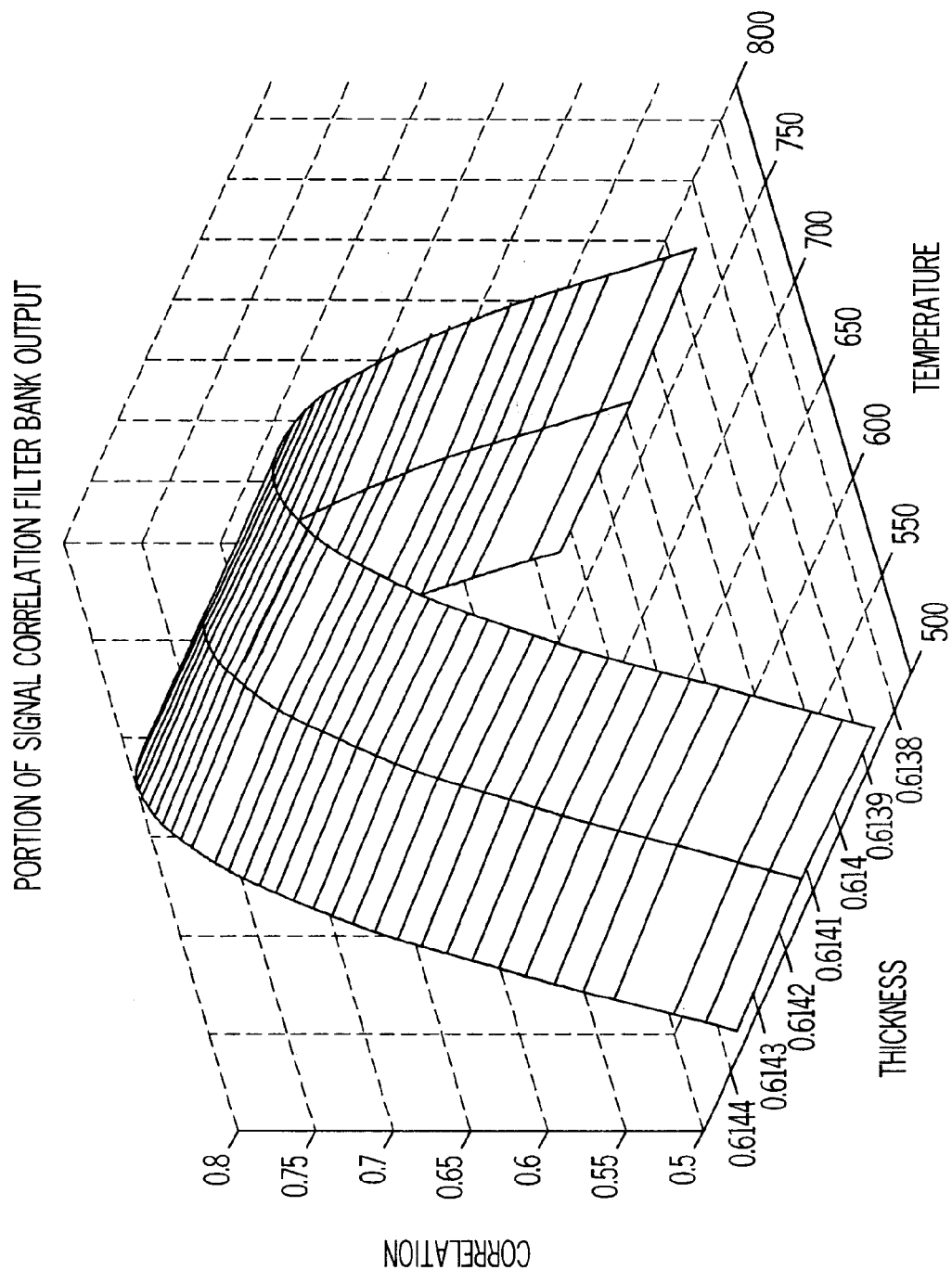
FIGS. 12A–12C illustrate the output of the correlator, or filter-bank, of FIG. 4, the best match of which is used to determine the thickness and temperature of the material under scrutiny in accordance with the present invention.
Figure 12C:
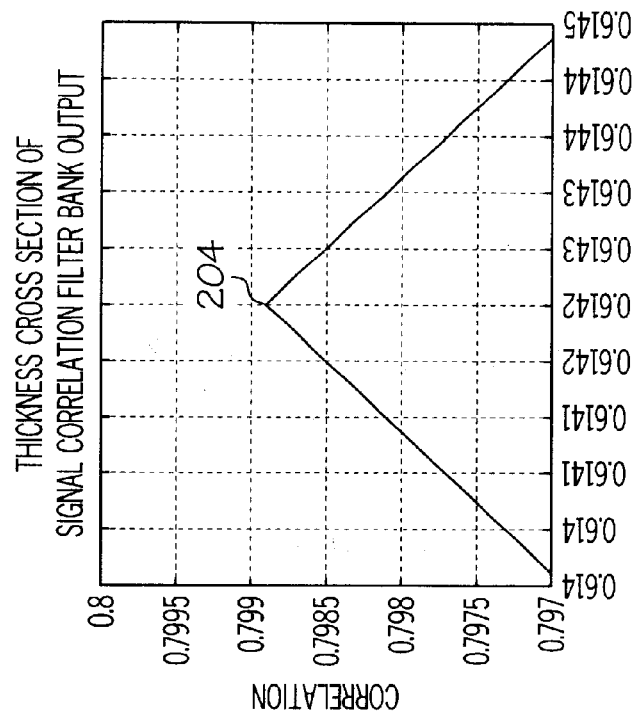
Figure 12B:
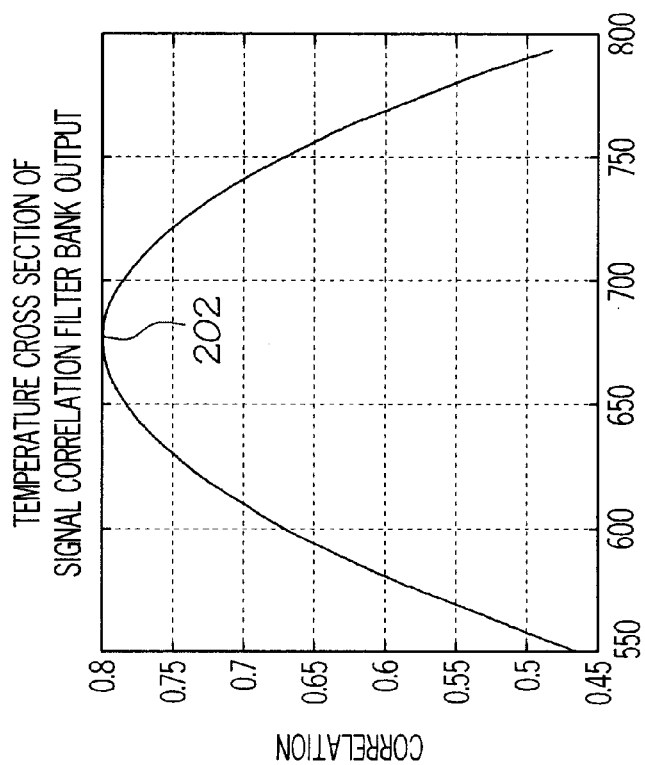

FIGS. 12A–12C illustrate the determination of correlation. In FIG. 12A, the degree of correlation is plotted as a function of material thickness and material temperature. In FIG. 12B, the temperature of the material is determined as the peak of correlation 202 between the measured signal 114 and theoretical signals in the matrix 112. Similarly, along the thickness dimension of FIG. 12C, the thickness of the material is determined as the peak of correlation 204. Other forms of correlation are possible, depending on the application.

Figure 13:
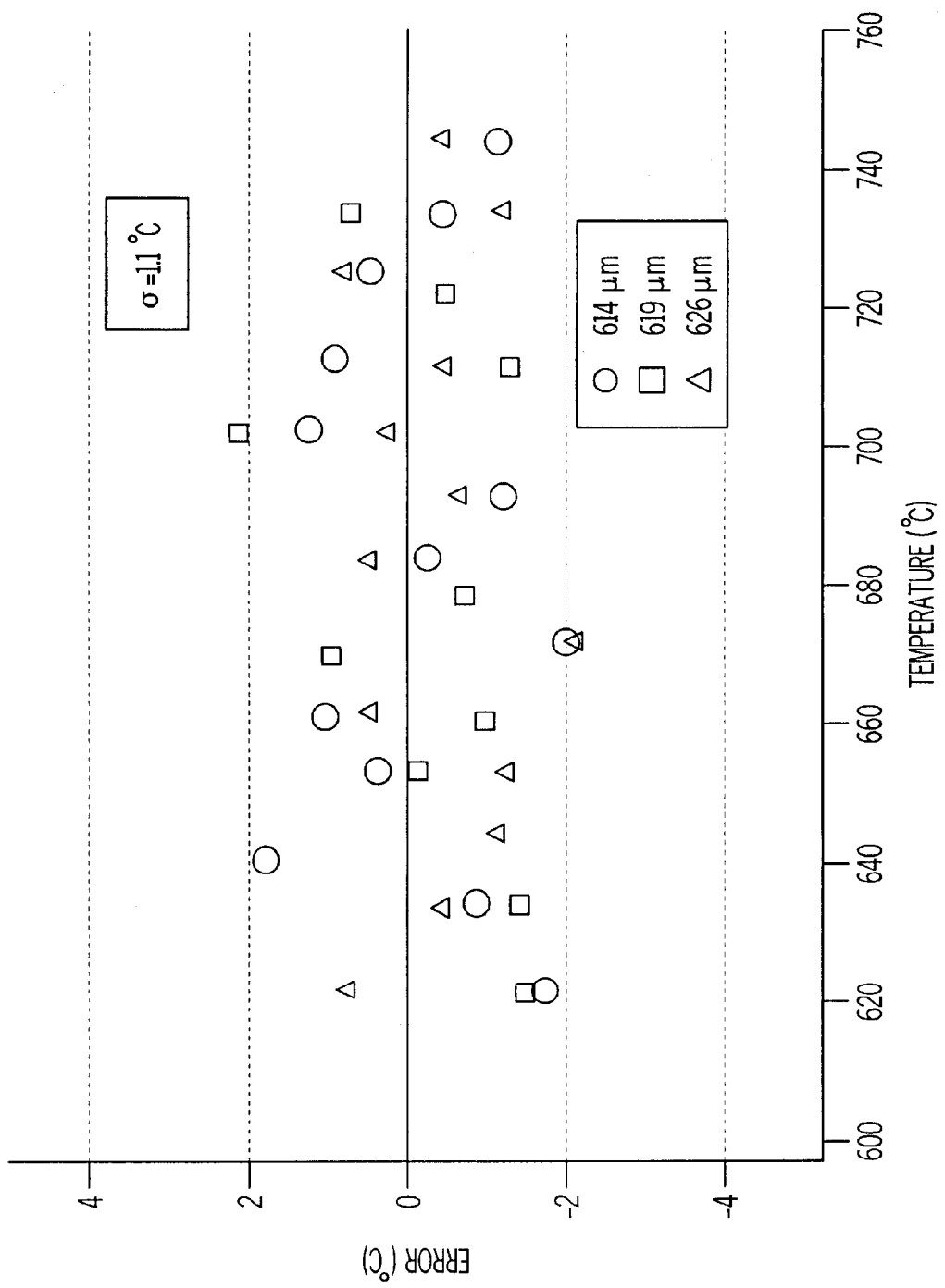
FIG. 13 is a chart of experimental results for three wafers of various thicknesses in accordance with the present invention.

FIG. 13 illustrates the error associated with utilizing the aforementioned technique for data collected on a range of silicon wafers indicative of industry-standard thickness variation. The experimental result of temperature measurement on three such wafers are illustrated. Results are accurate to 1.1 degrees at one standard deviation.

Although the above illustration uses temperature as an example, other material properties could be determined. For example, in the above illustration, the elastic constants search space was simplified to a single parameter of temperature. If the elastic constants were variable, the search space could be expanded to search over a realistic combination of elastic constants and thickness, instead of temperature and thickness. The summation of plane waves, in conjunction with the iterative wavelet technique used to characterize the transduction event appears to be a sufficient model for temperature measurement. This method of interrogation analysis is applicable to any arbitrarily-oriented anisotropic thin layer material.

Note that for purposes of the present invention, the term "anisotropic" includes all crystalline and non-crystalline materials. Isotropic, or single crystal, materials wherein the crystal axes are substantially aligned, is, for purposes of the present invention, a special case of anisotropic. The present invention is equally applicable to both isotropic and anisotropic materials.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for generating theoretical functions to characterize a material property value of a thin anisotropic material comprising:

generating a model of the thin material comprising the behavior of material physical parameters as functions of the material property value to be characterized;

for a plurality of known material thicknesses and known material property values:

simulating a transduction mechanism at a source location for generating a simulated elastic stress wave operating on the model at a plurality of source locations;

computing the simulated intensities of signals generated by the simulated elastic stress waves at a sense location to provide a composite signal; and computing theoretical functions from the composite signal at each thickness and each material property value; and applying the theoretical functions to a measured signal of an elastic stress wave generated in an unknown material to determine a material property value of the unknown material.

2. The method of claim 1 wherein the step of applying the theoretical functions to a measured signal of an elastic stress wave comprises:

following determination of the theoretical functions, generating an elastic stress wave in a material of unknown thickness and unknown material property value at a source location; and sensing the intensity of a measured signal generated by the elastic stress wave at a sense location positioned a known distance from the source location;

correlating the measured signal to the theoretical functions to determine correlation values; and determining a material thickness value and material property value based on best correlation values.

3. The method of claim 2 wherein correlating comprises pattern recognition.

4. The method of claim 1 wherein the transduction mechanism comprises a simulation of ring excitation comprising a plurality of line excitations arranged tangentially about a ring.

5. The method of claim 1 wherein the material property comprises a property selected from the group consisting of: temperature, hardness, elastic constants, density, composition, crystal orientation, grain size, pressure, and residual stress.

6. The method of claim 1 wherein the theoretical signals comprise a matrix of modal excitation functions.

7. The method of claim 1 wherein the physical parameters comprise elastic constants and density of the material.

8. The method of claim 1 wherein the theoretical functions are computed for symmetric modes and antisymmetric modes.

9. The method of claim 1 wherein simulating a transduction event comprises an empirical characterization of a transduction event in a material comprising:

initiating a transduction event in a material to generate a measured signal;

propagating an initial estimate of the transduction event along known dispersion curves characterizing the material to generate a theoretical signal;

decomposing the measured and theoretical signals and determining their respective amplitudes along the dispersion curves;

comparing the decomposed measured and theoretical signals to generate an error signal; and modifying the initial estimate by the error signal.

10. The method of claim 9 wherein propagating and decomposing are performed along a plurality of orientations relative to the material crystal axis.

11. The method of claim 9 wherein decomposing comprises at least one decomposing technique selected from the group consisting of: continuous wavelet transform, short-time Fourier transform, Wigner-Ville transform, and Choi-Williams transform.

12. The method of claim 9 wherein the measured and theoretical signals each comprise symmetric and antisymmetric modes of propagation.

13. The method of claim 9 wherein propagating, decomposing, comparing and modifying are performed iteratively until the error signal is within predetermined limits.

14. The method of claim 9 further comprising time-shifting the theoretical signal with respect to the measured signal such that they are contemporaneous.

15. The method of claim 9 wherein decomposing and determining further comprises determining the average respective amplitudes of the measured and theoretical signals along the dispersion curves.

16. A method for empirical characterization of a transduction event in a material comprising:

initiating a transduction event in a material to generate a measured signal;

propagating an initial estimate of the transduction event along known dispersion curves characterizing the material to generate a theoretical signal;

decomposing the measured and theoretical signals and determining their respective amplitudes along the dispersion curves;

comparing the decomposed measured and theoretical signals to generate an error signal; and modifying the initial estimate by the error signal.

17. The method of claim 16 wherein the material is a thin anisotropic material.

18. The method of claim 16 wherein the material is of unknown thickness.

19. The method of claim 16 wherein propagating and decomposing are performed along a plurality of orientations relative to the material crystal axis.

20. The method of claim 16 wherein decomposing comprises at least one decomposing technique selected from the group consisting of: continuous wavelet transform, short-time Fourier transform, Wigner-Ville transform, and Choi-Williams transform.

21. The method of claim 16 wherein the measured and theoretical signals each comprise symmetric and antisymmetric modes of propagation.

22. The method of claim 16 wherein propagating, decomposing, comparing and modifying are performed iteratively until the error signal is within predetermined limits.

23. The method of claim 16 further comprising time-shifting the theoretical signal with respect to the measured signal such that they are contemporaneous.

24. The method of claim 16 wherein decomposing and determining further comprises determining the average respective amplitudes of the measured and theoretical signals along the dispersion curves.

25. A system for generating theoretical functions to characterize a material property value of a thin anisotropic material comprising:

means for generating a model of the thin material comprising the behavior of material physical parameters as functions of the material property value to be characterized;

means for simulating a transduction mechanism at a source location for generating a simulated elastic stress wave operating on the model at a plurality of source locations for a plurality of known material thicknesses and known material property values;

means for computing the simulated intensities of signals generated by the simulated elastic stress waves at a sense location to provide a composite signal;

means for computing theoretical functions from the composite signal at each thickness and each material property value; and means for applying the theoretical functions to a measured signal of an elastic stress wave generated in an unknown material to determine a material property value of the unknown material.

26. The system of claim 25 wherein the means for applying the theoretical functions to a measured signal of an elastic stress wave further comprises:

means for generating an elastic stress wave in a material of unknown thickness and unknown material property value at a source location; and means for sensing the intensity of a measured signal generated by the elastic stress wave at a sense location positioned a known distance from the source location;

means for correlating the measured signal to the theoretical functions to determine correlation values; and means for determining a material thickness value and material property value based on best correlation values.

27. The system of claim 26 wherein the means for correlating comprises pattern recognition means.

28. The system of claim 25 wherein the transduction mechanism comprises a simulation of ring excitation comprising a plurality of line excitations arranged tangentially about a ring.

29. The system of claim 25 wherein the material property comprises a property selected from the group consisting of: temperature, hardness, elastic constants, density, composition, crystal orientation, grain size, pressure, and residual stress.

30. The system of claim 25 wherein the theoretical signals comprise a matrix of modal excitation functions.

31. The system of claim 25 wherein the physical parameters comprise elastic constants and density of the material.

32. The system of claim 25 wherein the theoretical functions are computed for symmetric modes and antisymmetric modes.

33. The system of claim 25 wherein the means for simulating a transduction event comprises an empirical characterization of a transduction event in a material comprising:

means for initiating a transduction event in a material to generate a measured signal;

means for propagating an initial estimate of the transduction event along known dispersion curves characterizing the material to generate a theoretical signal;

means for decomposing the measured and theoretical signals and determining their respective amplitudes along the dispersion curves;

means for comparing the decomposed measured and theoretical signals to generate an error signal; and means for modifying the initial estimate by the error signal.

34. The system of claim 33 wherein the means for propagating and means for decomposing propagate and decompose along a plurality of orientations relative to the material crystal axis.

35. The system of claim 33 wherein the means for decomposing comprises at least one decomposing technique selected from the group consisting of: continuous wavelet transform, short-time Fourier transform, Wigner-Ville transform, and Choi-Williams transform.

36. The system of claim 33 wherein the measured and theoretical signals each comprise symmetric and antisymmetric modes of propagation.

37. The system of claim 33 wherein the means for propagating, means for decomposing, means for comparing, and means for modifying operate iteratively until the error signal is within predetermined limits.

38. The system of claim 33 further comprising means for time-shifting the theoretical signal with respect to the measured signal such that they are contemporaneous.

39. The system of claim 33 wherein the means for decomposing and determining further determines the average respective amplitudes of the measured and theoretical signals along the dispersion curves.

40. A system for empirical characterization of a transduction event in a material comprising:

means for initiating a transduction event in a material to generate a measured signal;

means for propagating an initial estimate of the transduction event along known dispersion curves characterizing the material to generate a theoretical signal;

means for decomposing the measured and theoretical signals and determining their respective amplitudes along the dispersion curves;

means for comparing the decomposed measured and theoretical signals to generate an error signal; and means for modifying the initial estimate by the error signal.

41. The system of claim 40 wherein the material is a thin anisotropic material.

42. The system of claim 40 wherein the material is of unknown thickness.

43. The system of claim 40 wherein the means for propagating and decomposing propagates and decomposes along a plurality of orientations relative to the material crystal axis.

44. The system of claim 40 wherein the means for decomposing comprises at least one decomposing technique selected from the group consisting of: continuous wavelet transform, short-time Fourier transform, Wigner-Ville transform, and Choi-Williams transform.

45. The system of claim 40 wherein the measured and theoretical signals each comprise symmetric and antisymmetric modes of propagation.

46. The system of claim 40 wherein the means for propagating, means for decomposing, means for comparing, and means for modifying operate iteratively until the error signal is within predetermined limits.

47. The system of claim 40 further comprising means for time-shifting the theoretical signal with respect to the measured signal such that they are contemporaneous.

48. The system of claim 40 wherein the means for decomposing and determining further comprises means for determining the average respective amplitudes of the measured and theoretical signals along the dispersion curves.

* * * * *